United States Patent
Touleimat et al.

(10) Patent No.: US 8,840,670 B2
(45) Date of Patent: Sep. 23, 2014

(54) ADJUSTABLE MANDIBLE JOINT SYSTEM

(76) Inventors: Saad Touleimat, Newark, NJ (US); Abdul-Elah Touleimat, Newark, NJ (US)

( * ) Notice: Subject to any disclaimer, the term of this patent is extended or adjusted under 35 U.S.C. 154(b) by 0 days.

(21) Appl. No.: 13/493,301

(22) Filed: Jun. 11, 2012

(65) Prior Publication Data
US 2013/0331944 A1    Dec. 12, 2013

(51) Int. Cl.
*A61F 2/02* (2006.01)
(52) U.S. Cl.
USPC ............................................. 623/17.17
(58) Field of Classification Search
USPC ........................................... 623/17.17–17.19
See application file for complete search history.

(56) References Cited

U.S. PATENT DOCUMENTS

| | | | |
|---|---|---|---|
| 5,549,680 A | | 8/1996 | Gordon |
| 5,885,283 A | * | 3/1999 | Gittleman .................. 606/57 |
| 5,989,292 A | | 11/1999 | Van Loon |
| 7,601,175 B2 | | 10/2009 | Feigenwinter et al. |
| 7,883,544 B2 | | 2/2011 | Feigenwinter et al. |

OTHER PUBLICATIONS

"TMJ Concepts", www.tmjconcepts.com, accessed Oct. 28, 2011.

* cited by examiner

*Primary Examiner* — David Isabella
*Assistant Examiner* — Ann Schillinger
(74) *Attorney, Agent, or Firm* — Michael J. Feigin, Esq.; Feigin & Associates, LLC

(57) ABSTRACT

The presently disclosed technology is directed towards an adjustable prosthesis for replacing a mandible along with the ramus with a mandibular condyle. The prosthesis articulates to the skull at the temporal bone region. The prosthesis, of embodiments of the disclosed technology, has a horizontal/sagittal (or generally horizontal) and/or vertical (or generally vertical) adjustment screw which is accessible after implantation. In one embodiment, the adjustment screw is accessible by way of using a tool and rotating an adjustment rod. The adjustment rod is accessed via a sub-periosteal intra-oral incision, through points in the oral cavity post-surgical placement. The adjustment rod allows the length of the device, both a horizontal portion and vertical portion, to be adjusted post-placement.

8 Claims, 9 Drawing Sheets

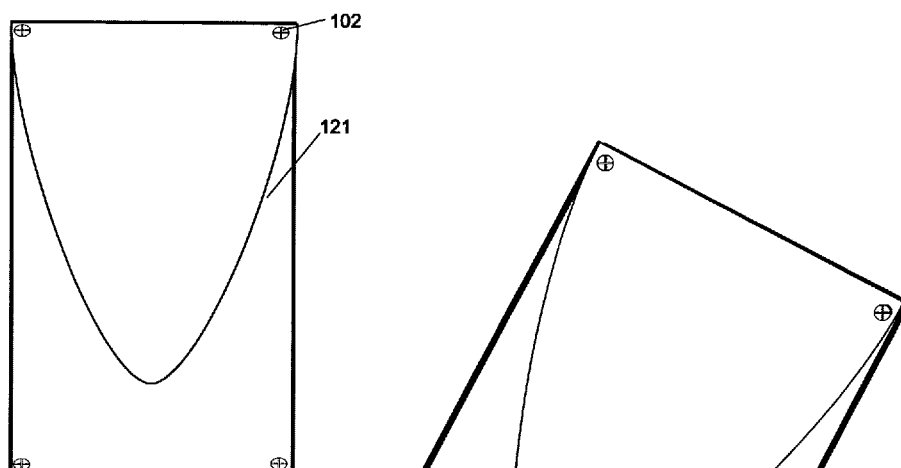
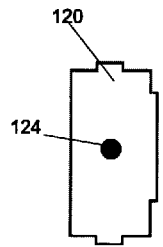
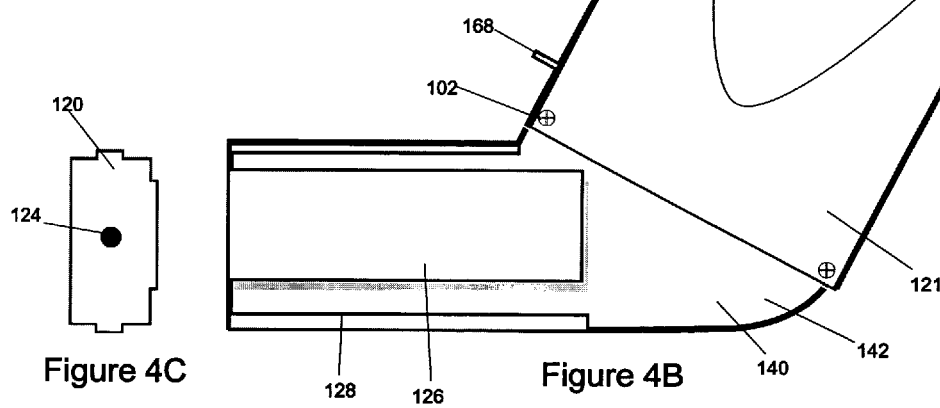
Figure 4A
Figure 4C
Figure 4B

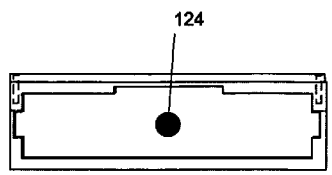
Figure 5A
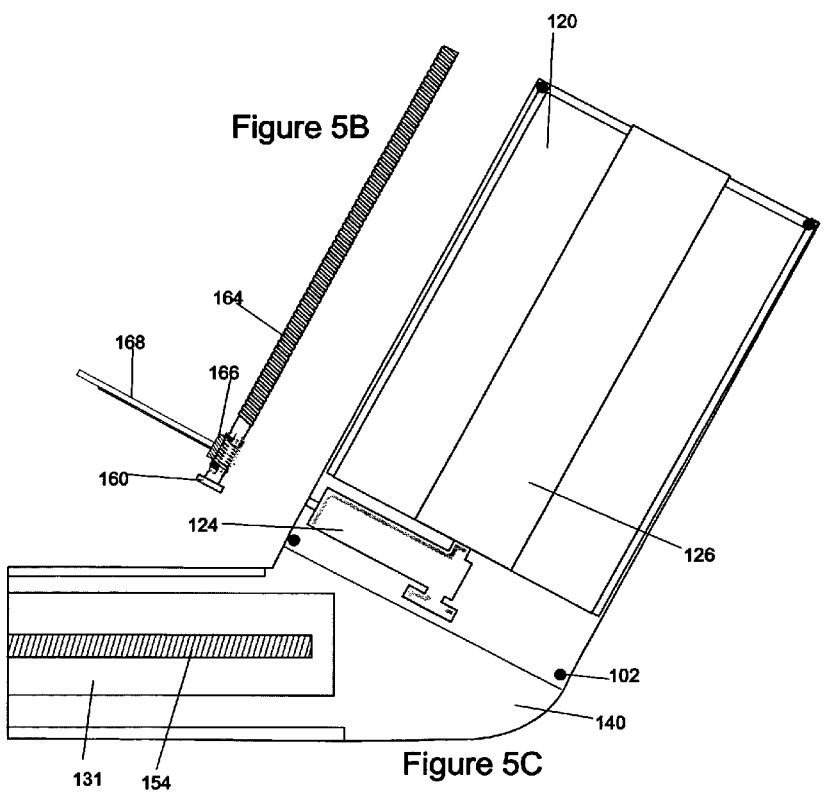
Figure 5B
Figure 5C
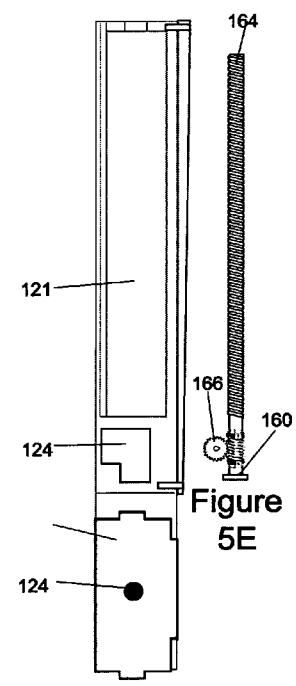
Figure 5E
Figure 5D

ADJUSTABLE MANDIBLE JOINT SYSTEM

FIELD OF THE DISCLOSED TECHNOLOGY

The disclosed technology is geared generally towards Artificial Joints. More specifically, the disclosed technology relates to adjustable artificial joint.

BACKGROUND OF THE DISCLOSED TECHNOLOGY

Total temporomandibular joint (TMJ) replacement occurs in the art when the TMJ has become damaged, infected, resorbed, ankylosed or was formed in a defective manner or even haven't formed at all. Each human has two joints that arise from the lower jaw (mandible) and articulates with the skull at the temporal bone. Therefore, this joint is called "the temporomandibular joint" or TMJ. Several muscles are attached simultaneously to the mandible and the skull. Throughout synchronized movements of these muscles (extension or contraction), movement of the mandible is possible, and thus a human is able to open and close his/her mouth.

In the facial skeleton, the temporomandibular joint serves as an important local facial growth center. In people with a healthy and properly functioning temporomandibular joint, this joint is the center in which the lateral side of the face grows in all three dimensions (height, width, and depth). Therefore, any disturbance; trauma; neoplasm; or even congenital abnormality to the joint—and particularly the mandibular condyle—will cause disturbance of the growth to the face.

In conclusion: the TMJ not only provides the normal hinge/sliding movement of the lower jaw, but also serves as a local growth center of the face.

More specifically, describing the anatomy, which is useful in understanding the technology presented herein, there are two TMJs, one on either side of the mandible/face. The name is derived from the two bones which form the joint: the ramus (referred to herein as the "generally vertical" or "vertical portion," for convenience) and the body of the mandible (referred to herein as the "generally horizontal" or "horizontal portion". The unique feature of the TMJs is the articular disc. The disc is composed of fibrocartilagenous tissue (like the firm and flexible elastic cartilage of the ear) which is positioned between the two bones that form the joint. The TMJs are one of the few synovial joints in the human body with an articular disc, another being the sternoclavicular joint. The disc divides each joint into two. The lower joint compartment formed by the mandible and the articular disc is involved in rotational movement—this is the initial movement of the jaw when the mouth opens. The upper joint compartment formed by the articular disk and the temporal bone is involved in translational movement—this is the secondary gliding motion of the jaw as it is opened widely. The part of the mandible which mates to the under-surface of the disc is the condyle, and the part of the temporal bone which mates to the upper surface of the disk is the glenoid (or mandibular) fossa.

The surfaces in contact with one another (bone and cartilage) do not have any receptors to transmit the feeling of pain. The pain therefore originates from one of the surrounding soft tissues, from the posterior part of the disc, or from the trigeminal nerve itself, which provides innervations to the joint area. When receptors from one of these areas are triggered, the pain can cause a reflex to limit the mandible's movement. Furthermore, inflammation of the joints or damage to the trigeminal nerve can cause constant pain, even without movement of the jaw.

In the field of cranio/maxillo/facial/re-constructive surgery, an artificial temporomandibular joint device may be used to replace a diseased TMJ which is damaged beyond repair or not biologically/physiologically functioning. Prior art TMJ prosthesis, such as those disclosed at tmjconcepts.com, at the time of this writing, include a metal condyle made from cobalt-chromium-molybdenum, and a metal prosthesis made from a titanium alloy, anchored to the lower jaw with titanium alloy screws. In the prior art, the component attaching to bone (fossa component) "has a durable medical-grade plastic surface made from ultra-high-molecular-weight polyethylene (also known as UHMWPE). This is attached to a metal backing made from pure titanium. This component is anchored to the skull with titanium alloy screws." Such prior art prosthesis are shaped to fit a particular skull and lower jaw.

Again, as disclosed on tmjconcepts.com, the method of prosthesising is as follows, in the prior art: 1) Computed axial tomography (CAT scan) of the jaw region, 2) construction of an anatomical bone, 3) review by a surgeon, 4) surgical prosthesis placement. With the patient under general anesthesia, and using two incisions, the components are surgically placed—the condylar component is placed through an incision below and behind the lower jaw, and the fossa component is prosthesised through an incision in front of the ear.

The problem with such prosthetic devices, as written on tmjconcepts.com at the time of filing this application, is as follows: "Despite the fact that these implants are fitted specifically to your anatomy, you should not expect them to last for a lifetime. While the expected life of a TMJ implant is difficult to estimate, it is finite and may significantly differ for each patient due to the diversity of conditions seen in TMJ reconstruction." Thus, the problem known in the art is that the implants are fitted for a particular person, with a particular size. This is especially problematic in the case of a growing person (a child), one healing from an accident (whose anatomy is likely to change), and the like. The shape and size of a person is bound to change slowly over time, while the prosthesis will not. This causes the person's face to be uneven, or worse, and will necessitate another surgical procedure to replace the prosthetic device, including removing the first prosthesis, and screws through the bone, and placing a new prosthesis with new fixation points. This is, obviously, undesirable because it requires additional invasive surgical procedures, increases the risk of failure, and decreases mouth opening ability due to increased scarring of the area. As the patient is required to undergo additional surgical procedures, this also increases costs and recovery time.

It is therefore an object of the disclosed technology to provide a TMJ surgical prosthesis which is more versatile than the prior art, and which may remain in place, despite changes in the anatomy of a person receiving the prosthesis.

SUMMARY OF THE DISCLOSED TECHNOLOGY

It is therefore an object of the disclosed technology to 1) provide the needy patient with an artificial temporomandibular joint device; 2) provide the surgeon with the option to change the dimensions of the temporomandibular joint/mandible to accommodate or match the dimensions of the joint/mandible on the other, non-effected, side; and 3) stimulate and simulate the biological function of the normal temporomandibular joint/condyle in which this device will act by changing its dimensions to simulate the normal local growth center.

The disclosed technology described herein addresses a need, unfulfilled in the prior art by allowing one to access and adjust an prosthesis as part of a post-operative procedure(s).

In a first embodiment of the disclosed technology, a treating surgeon modifies the dimensions of a specialized prosthesis post operatively through the placement of a small intra-oral incision, to gain access to the device, as needed. Such an incision is placed inside the mouth, therefore avoiding an undesirable facial skin scars. The incision is placed in the lateral posterior aspect of the mandible at the third molar/external oblique ridge area which is about or between 2 or 3 cm posterior to the third molar. In alternative embodiments, this position may be anywhere within the mouth of the patient, granting access to the prosthesis. The incision reflects a full thickness subperiosteal flap to access the lateral side of the mandible where the adjustment screws of the device are located inferior/posterior to the access flap. The device, in embodiments, is fixated to the mandible using an intra-osseous bone plates and screws. A portion of the device corresponding to a portion of the mandible being replaced by the corresponding portion of the prosthesis, has a threaded, elongated member, such as a screw with stop, within such a portion of the prosthesis. There is further a gear functionally engaged between the adjustment mechanism and the threaded, elongated member arranged such that when the adjustment mechanism is rotated, the threaded, elongated member is rotated and an overall length or width of the portion of the prosthesis corresponding to the portion of the mandible is increased or decreased.

In embodiments, the prosthesis device has a vertical or sagital expansion piece or combination of both and capability in which it is indicated for patients who are anticipated to need or want stimulated growth of the mandible in one, mainly vertical, direction. Another device permits vertical and sagital expansion, for patients anticipated or needing mandibular growth in both planes. There may be multiple such portions of the prosthesis Each may have a separate adjustment mechanism for adjusting the length thereof, each adjustment mechanism adjusted via intra-oral submucosal access.

At least one socket plate adapted for articulation of the prosthesis to bone, and a ball joint engaged with the socket plate and the portion of the prosthesis corresponding to the portion of the mandible being replaced, is employed in an embodiment of the disclosed technology. The ball joint may be adapted to allow rotation of the portion of the prosthesis, with respect to the socket plate.

The threaded, elongated member may have a worm screw engaged with the gear, the gear being fixed to an elongated shaft of the adjustment mechanism. Upon rotation of the elongated shaft, the worm gear and the threaded, elongated member rotate transverse to the direction of rotation of the elongated shaft. A portion of the threaded shaft is housed within an outer housing of the prosthesis, in an embodiment of the disclosed technology, and rotation of the threaded shaft causes the outer housing to move nearer or further away from another portion of the prosthesis, to which the threaded shaft is threadedly engaged. A stop, on the elongated, threaded member, in an embodiment of the disclosed technology, forms a unitary structure with the threaded shaft, and the stop and a portion of the elongated shaft are held in place inside a cavity of the outer housing during elongation of the prosthesis.

In one embodiment, a diagonal portion corresponding to a ramus with adjustable screw therein, and lateral portion corresponding to a body of the mandible, an adjustable screw therein, has a unitary plate extending the length of the lateral portion (in a fully retracted configuration) and extending through a mid-portion corresponding at least to a medically defined angle of the mandible. A first adjustable screw extends a housing of the diagonal portion past an elongated, planar surface of the unitary plate, and a second adjustable screw extends a housing of the lower portion past an elongated, planar surface of the unitary plate. Each housing has a first cavity comprising a majority of the elongated, threaded member therein, in embodiments, of the disclosed technology. A second cavity, in embodiments, has an internal area adapted to retain a stop of the elongated, threaded member therein, and consists of two portals, a first adapted for passage there-through of the elongated, threaded member, and a second adapted for passage there-through of an adjustment mechanism.

In a method of using the device of the disclosed technology, one attaches, via an upper socket plate and/or lower reconstruction plate, a prosthesis to existing bone, the prosthesis comprising a lower and upper piece. Either before and/or after the previous step (that is, pre- and/or post-operative), one angles the upper piece by way of a joint connecting the upper piece to the upper socket plate, and then or precedented, adjusts a length of the upper piece of the prosthesis, post-placement, by way of an adjustment screw extending submucosally from the upper piece. In a further step, one may adjust a length of the lower piece of the prosthesis, post-placement, by way of a second adjustment screw extending submucosally from the lower piece. The adjustment screw(s) are accessible, in embodiments of the disclosed technology, via an intra-oral incision to be made by a surgeon. The dimensions of the device are adjusted due to the controlled expansion of the device that the treating surgeon will perform post operatively (post placement), in a fashion that will either correspond/match the amount of growth that the patient exhibited on the other side, or in a desired amount of growth the surgeon wants to stimulate.

The prosthesis adjustment mechanism used has a threaded screw threadedly attached to a second housing of the prosthesis on a first end, the threaded screw having a stop housed within a first housing. A toothed gear rotatably engages with a worm gear of the adjustment screw. An adjustment screw extends perpendicular to an elongated plane of the threaded screw, the adjustment screw being accessible intraorally via an intra-oral incision. A second prosthesis adjustment mechanism may be used, the first being functionally engaged with the height of the lower jaw, and the second beign functionally engaged with the depth/width of the lower jaw replacement. An inner cavity may hold the stop, the worm gear, and the toothed gear, and an outer cavity holds the threads of the threaded screw therein. A plate situated between the upper and the lower place extends a length of the prosthesis, causing a portion of the plate to exit from a the outer cavity when the adjustment screw is rotated.

BRIEF DESCRIPTION OF THE DRAWINGS

FIG. 4A is a side view of a cover of a vertical (upper) portion of an adjustable joint of embodiments of the disclosed technology.

FIG. 4B is a side view of the vertical portion of the adjustable joint of FIG. 4A.

FIG. 4C is a top view of the vertical portion of the adjustable joint of FIG. 4B.

FIG. 5A shows a top view of the vertical portion of the adjustable joint, in an embodiment of the disclosed technology.

FIG. 5B is a side view of a vertical screw of an embodiment of the disclosed technology, aligned with a corresponding receptacle of FIG. 5C.

FIG. 5C is a side cutaway view of the vertical portion of the adjustable joint of FIG. 4B.

FIG. 5D is a side cutaway view of the vertical portion of the adjustable joint, turned 90 degrees with respect to FIG. 5C.

FIG. 5E is a side view of the vertical screw of FIG. 5B, aligned with the corresponding receptacle and orientation shown with references to the adjacently pictured FIG. 5D.

Figure 1A:
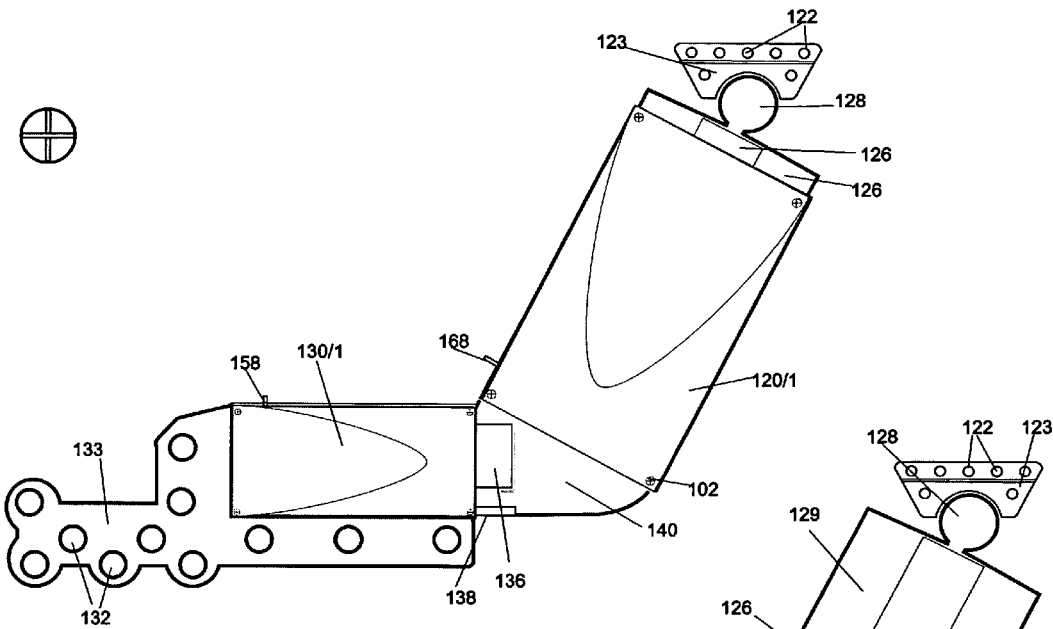
FIG. 1A is a side view of an adjustable joint of an embodiment of the disclosed technology, in a fully closed configuration.

A better understanding of the disclosed technology will be obtained from the following detailed description of embodiments of the disclosed technology taken in conjunction with the drawings.

DETAILED DESCRIPTION OF EMBODIMENTS OF THE DISCLOSED TECHNOLOGY

The presently disclosed technology is directed towards an adjustable temporomandibular joint prosthesis adapted for restoring and replacing a diseased temporomandibular joint with the ability to adjust the dimensions of the prosthesis to accommodate/stimulate the need/desire of an prosthesised temporomandibular joint for specific indications, such as in growing children. The prosthesis articulates with the skull with a basic ball and socket joint, at an upper and/or lower region of the mandible, such as at the condylar process of the mandible, ramus, body/angle of the mandible. In this disclosure, "generally" is defined as "close to an ordinal direction such that it would be described as such by a person having ordinary skill in the art." Thus, "generally horizontal" should be understood as being closest to the horizontal ordinal direction.

The prosthesis, of embodiments of the disclosed technology, has a horizontal (or generally horizontal) and/or vertical (or generally vertical) adjustment screw which is accessible after placement. In one embodiment, the adjustment screw is accessible by way of using a tool and rotating an adjustment rod. The adjustment rod is accessed intra orally, through a full thickness flap in the oral cavity post-surgery. The adjustment rod allows the length of the device, both a horizontal portion and vertical portion, to be adjusted post-prosthesisation. It should be understood that the horizontal portion corresponds to the lower jaw growth in a sagittal plane, and the vertical portion is used to describe the portion extending from the ramus/condylar process, or replaces any one of, or a plurality of, the condylar process, the ramus, and/or the coronoid process of the mandible. That is, the vertical portion of the prosthesis replaces one or more of these portions of the mandible, in addition to the TMJ structure, while the horizontal portion replaces the body of the lower jaw, and a portion thereof is also used for fixation to the mandible itself.

It should further be understood that the prosthesis device placed into a person is surgically placed via endaural and modified risdon incisions, in an embodiment of the disclosed technology. The prosthesis is made from biologically accepted metal such as titanium or vitalium, however, the articulating surface of the upper part may be made of other materials. The angle of the prosthesis, that is, the angle between upper and lower portions may vary from between 90 to 150 degrees and may be custom made based on three dimensional cat scans or other scans of the person. The dimensions and angulations can be fabricated after measuring the healthy side of the mandible/joint.

Embodiments of the disclosed technology will become clearer in view of the following description of the figures.

Figures 9A, 9B, 9C:
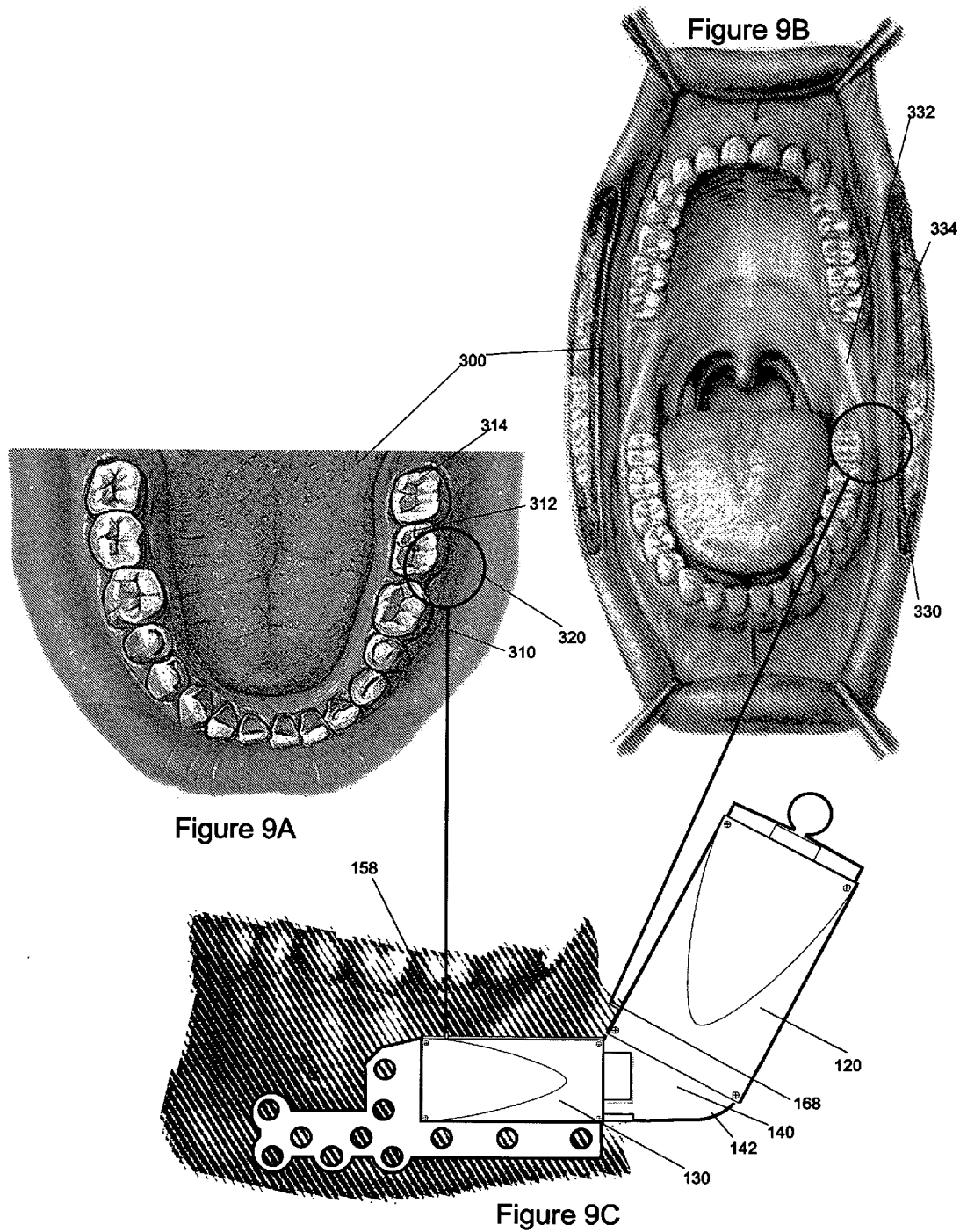
FIG. 9A shows a top view of the inside of a mouth with an access point used in an embodiment of the disclosed technology.
FIG. 9B shows the inside of a mouth with a second access point used in an embodiment of the disclosed technology.
FIG. 9C shows an orientation of the adjustable prosthesis with respect to a lower jaw, in an embodiment of the disclosed technology.

Skipping first to FIGS. 9 and 10, the device, as whole, will be described with reference to where the prosthesis is placed within a patient. FIG. 9C shows an orientation of the adjustable prosthesis with respect to a lower jaw, in an embodiment of the disclosed technology. The device has a generally vertical portion 120 and generally horizontal portion 130 (see definitions above). The generally vertical portion (actually, a diagonal portion), extends upwards, while the generally horizontal portion extends generally laterally/sagittally, with respect to a skull. The two portions 120 and 130 have an edge 142 at an adjoining section roughly corresponding to (defined as "having the function of, even when not in the exact position of") or corresponding to the angle of mandible that it is replacing. In this manner, the adjustable prosthesis extends generally laterally, vertically and sagitally, replacing both the generally lateral, horizontal and vertical portions of the mandible, or parts of one or both sections, as indicated for the patient. That is, a section of either the generally horizontal, vertical or sagittal portions, may be replaced, without replacing the any other portion, in embodiments of the disclosed technology.

Now referring to FIGS. 9A, 9B, and 9C, FIG. 9A shows a top view of the inside of a mouth with an access point used in an embodiment of the disclosed technology; FIG. 9B shows the inside of a mouth with a second access point used in an embodiment of the disclosed technology. FIG. 9C shows an orientation of the adjustable prosthesis with respect to a lower jaw, in an embodiment of the disclosed technology. The inside of the mouth 300 has a plurality of teeth (or places where, normally, teeth reside), including molars 312 and 314, as well as cheek 334 and connective tissue 332.

Upon prosthesisation of the generally horizontal prosthesis (or portion of an prosthesis) 130, an access point in the vicinity of circle 320 is created, between the teeth and the cheek, along the bottom of the interior of the mouth 300. More precisely, the access point (defined also as the point of entry for manipulation of the length of the prosthesis, post-prosthesisation) is located subperiosteal on the lateral side of the mandible. An intra-oral incision needs to be made, and a full thickness flap needs to be removed in an embodiment of a method of use of the device. After adjustment, the flap is repositioned in place and sutured. Upon prosthesisation of the generally vertical (diagonal) prosthesis (or portion of an prosthesis) 120, an access point is created in the vicinity of circle 330, along or near the bottom/back corner of the mouth 300. The distance from said corner is between about 1 and 5 cm, depending on the size of the mouth of the patient and/or size of the prosthesis. The position is along the third molar region. In other embodiments, the access point, for accessing the adjustment rod 158 or 168, is anywhere along the bottom or back portion of the mouth 300, extending through soft tissue from the prosthesis.

Figure 10:
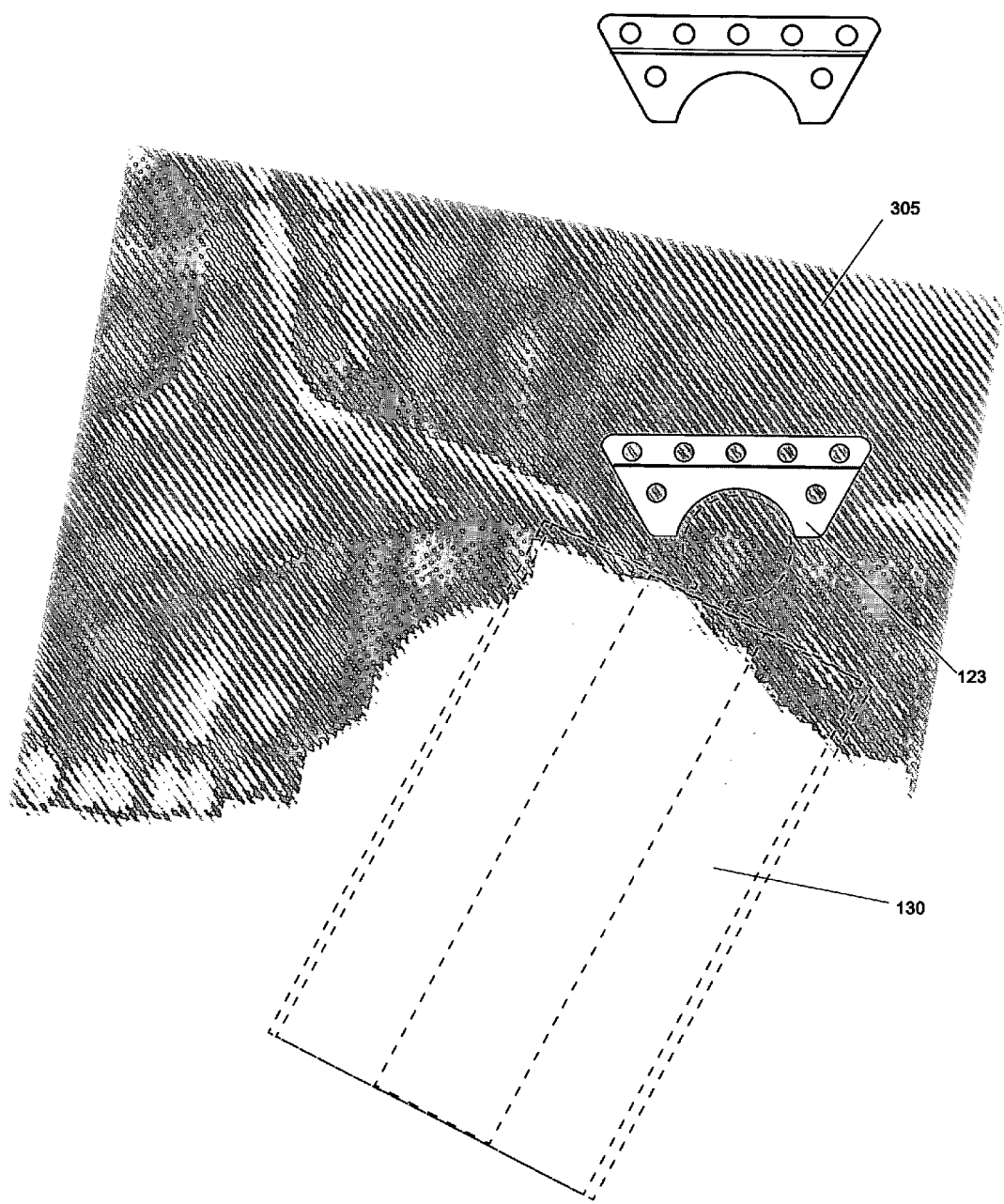
FIG. 10 shows the position of the adjustable device prosthesis with respect to a side view of a skull, in an embodiment of the disclosed technology.

FIG. 10 shows the position of the adjustable device prosthesis with respect to a side view of a skull, in an embodiment of the disclosed technology. The generally vertical prosthesis 130 of the adjustable prosthesis is shown in dotted lines, in position, articulates with the skull 305 with the upper socket plate 123. The ball of the generally vertical prosthesis portion 130 allows the generally vertical portion to rotate, with respect to the skull mimicking the movement of a normal TMJ.

Thus, based on the above description, it should be understood how the prosthesis is placed into the skull, as well as how the prosthesis is accessed to adjust same. Turning now to FIGS. 1-8, more precise mechanisms of the device will be described, showing the function (and best mode) of the prosthesis.

FIG. 1A is a side view of an adjustable joint of an embodiment of the disclosed technology, in a fully closed configuration. The upper socket plate 123 articulates to the temporal bone by way of portals 122 and corresponding bone screws. The jaw socket plate is the articulation between the prosthesis and the skull. Likewise, bone plate 133, which is fixedly attached to or an integral part (unitary structure) of the lower portion of the prosthesis 130 attaches to a lower portion of the jaw, by way of portals 132 for fastening devices, such as screws utilizing internal rigid fixation plates and screws principles. In embodiments of the disclosed technology, the socket plate 122 articulates with a ball joint 128 of the upper portion of the prosthesis 120 (it resembles the normal articulation between the mandible and the skull). The ball joint 128 allows the prosthesis to translate (rotate) about the pivot point between the ball 128 and socket plate 122, as needed during normal lower jaw movement, also during growth or change of the anatomy of the patient. Therefore, it allows for greater flexibility than the prior art when prosthesising the device, as the angle of attachment is variable. Still further, when installing two prosthesis (one on each side), it may be desired to adjust or change the length, if one side is unequal to the other side, even if each side is off only by millimeters.

Referring still to FIG. 1A, the upper portion of the prosthesis 120 (also referred to as the generally vertical or diagonal portion, corresponding to the ramus) has a covering 121 held on by screws or fasteners 102 (note: not all screws/fasteners are labeled for purposes of aesthetics in the figures, but it should be understood that all other plus symbols surrounded by circles in the figures represent screws or fasteners, and that the positions shown are but one embodiment, and are not meant to be limiting). Like the upper portion of the prosthesis, the lower portion of the prosthesis 130 has a covering 131. It should be understood that the configuration of the covers, dimensions and attachment mechanisms and shapes may vary from that shown, so long as the covers help determine the outer extremity of their respective portions of the prosthesis. The outer extremities of the device are generally designed or are designed to mimic the size, shape, texture, and at least the hardness (if not harder) than the bone being replaced. It should be understood that the coverings are taught by way of example, and not limitation and that each plate may be produced, in an alternative embodiment, comprising of a single, unitary piece.

Section 120 is the middle section of the prosthesis, which, depending on embodiment, is fixedly attached or integrated (forms a unitary structure) with either the top portion 120 or bottom portion 130. This middle portion, in an embodiment of the disclosed technology, shows a rounded lower side to mimic the angle of the mandible being replaced, this angle varies as does the angle of the normal lower jaw, such as between 90 and 150 degrees. The upper portion 120 and lower portion 130 "push off," that is, move with respect to this section. While the movement of each portion is relative with respect to other portions, for purposes of this disclosure, the movement of the upper and lower portions will be described relative to the position of the middle portion 140. By way of adjustment of the screws, the prosthesis may be elongated at the lower portion or upper portion. When such adjustment, the lower portion 130 moves away from the middle region 140. It is contemplated that the upper portion 120 moves away from the middle region 140, in another embodiment; however, in the figures shown, the upper portion 120 extends upwards from within, as shown in FIG. 1B.

Figure 1B:
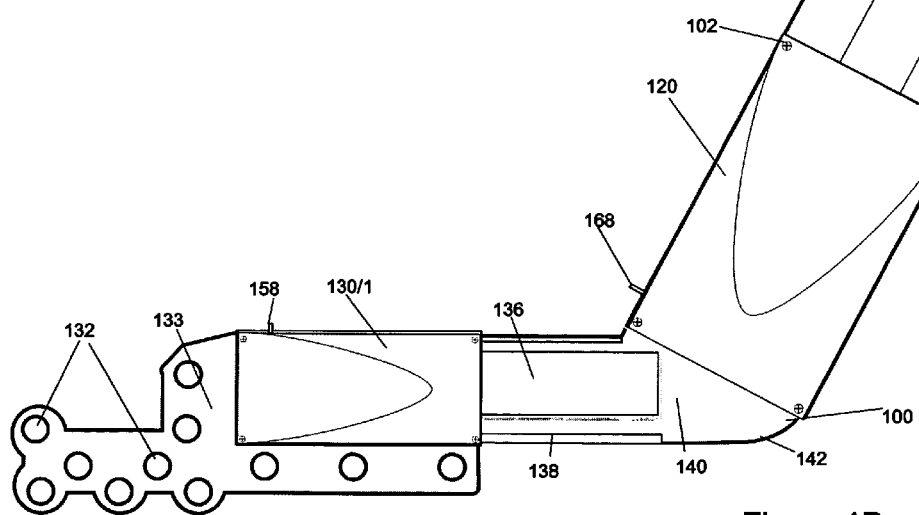
FIG. 1B is a side view of the adjustable joint of FIG. 1A, in a fully open configuration.

FIG. 1B is a side view of the adjustable joint of FIG. 1A, in a fully open configuration. Shaft 136 is now more visible, as is the dovetail 138. Similarly, shaft 126 is now more visible, as is also the interior plate 129. The shafts 136 and 126 are hollow, interior spaces adapted to comprise or contain an adjustable screw, and parts associated with such adjustable screws, as will be described beginning with reference to FIG. 3. When the screw is adjusted, by way of adjustment rod 158, the lower portion 130 moves away from the middle portion 140 (and the stationary back plate of/which forms the middle portion 140, with reference to the movement of lower piece 130, compared thereto). Likewise, when the screw is adjusted via adjustment rod 168, the plate 129 moves (diagonally) upwards/extends away from the housing 120. In either case, via external adjustment, pre-surgical placement and/or post-surgical placement, the extension of the device may be modified.

Figure 2:
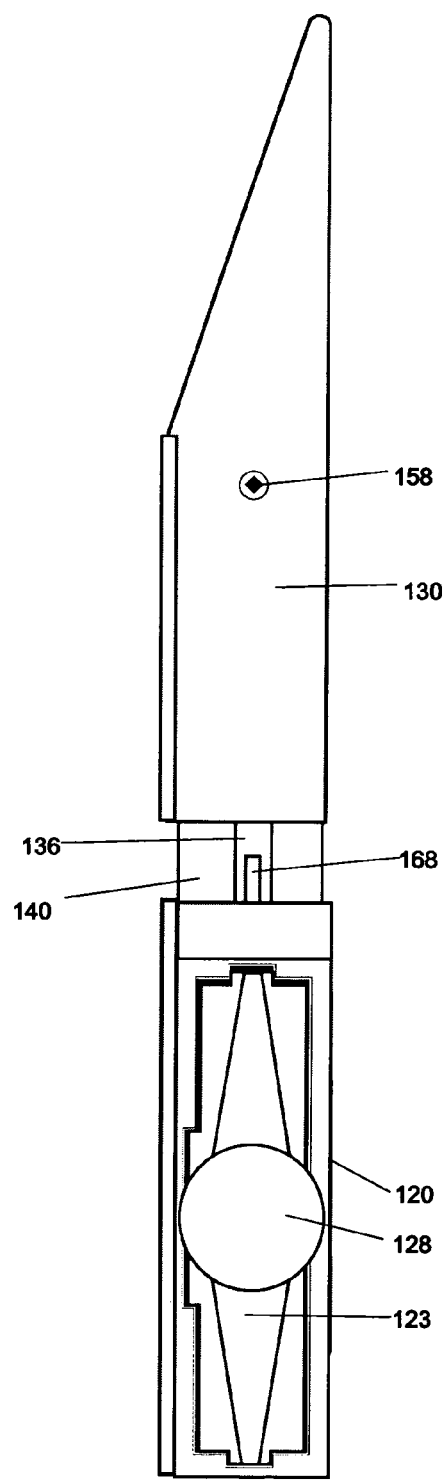
FIG. 2 is a top view of the adjustable joint of FIGS. 1A and 1B.

FIG. 2 is a top view of the adjustable joint of FIGS. 1A and 1B. The ball joint 128 is visible above the socket plate 123, situated above the upper portion 120 of the device, which in turn, is fixed to the central region or middle portion of the device 140. Adjustment rod 168 extends outwards, allowing for adjustment of a screw held therein, to extend or contract the upper portion 120, away or towards the middle portion. Similarly, adjustment rod 158 allows the lower housing 130 to move away from or towards the middle portion 140, by turning an adjustment screw within shaft 136.

Figure 3A:
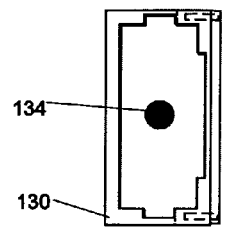
FIG. 3A is a top view of the lower housing of an adjustable joint of an embodiment of the disclosed technology.
Figure 3B:
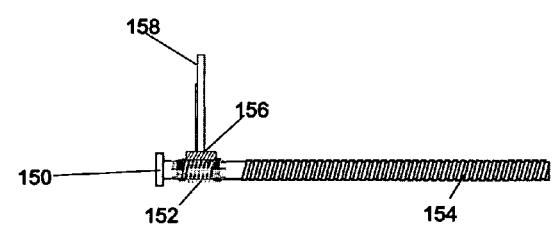
FIG. 3B is a side view of a horizontal adjustment screw of an embodiment of the disclosed technology, aligned with a corresponding receptacle of FIG. 3C.
Figure 3C:
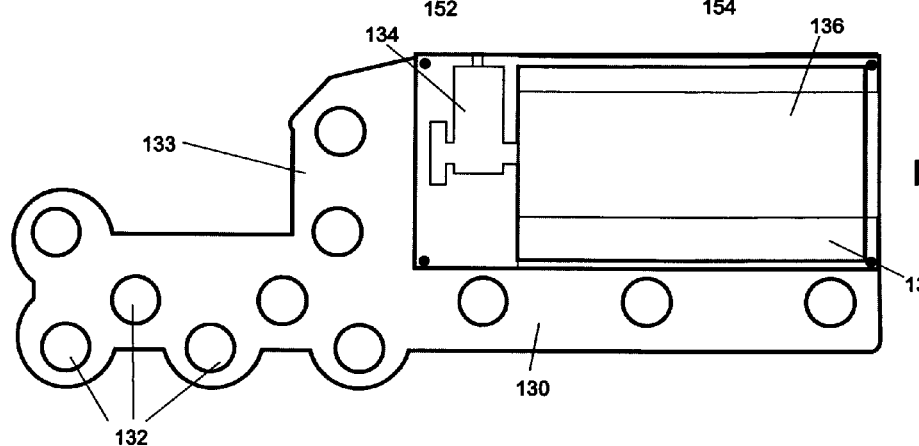
FIG. 3C is a side cutaway view of the horizontal (lower) portion of the adjustable joint of FIG. 3A.
Figure 3D:
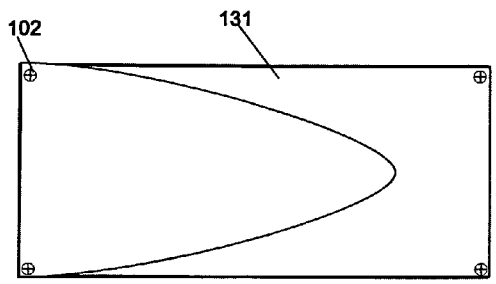
FIG. 3D is a side view of a cover of the horizontal portion of the adjustable joint of FIG. 3C.

Turning now to FIG. 3, followed by FIG. 6, showing the adjustment screw, FIG. 3A is a top view of the lower housing of an adjustable joint of an embodiment of the disclosed technology. FIG. 3B is a side view of a horizontal adjustment screw of an embodiment of the disclosed technology, aligned with a corresponding receptacle of FIG. 3C. FIG. 3C is a side cutaway view of the horizontal (lower) portion of the adjustable joint of FIG. 3A. FIG. 3D is a side view of a cover of the horizontal portion of the adjustable joint of FIG. 3C. In the lower housing, corresponding to the lower jaw, when surgically placed, in the cross-sectional view, one can see the bone plate 133 comprising a plurality of portals for fossa attachment between the lower portion 130 and bone of the patient. The lower piece 130 comprises a shaft 136, with dovetails 138 for slidable or fixed engagement with the housing cover 131. Inside the shaft, in embodiments of the disclosed technology, the adjustable screw is placed, the screw being shown in FIG. 3B. A head or stop of the screw 150 resides in the correspondingly shaped portion of the hollow interior of the piece 130. That is, an interior receptacle 134, or cave-like chasm forms a hollow opening within each piece 120 and 130 and is shaped for insertion of a screw head and associated parts. In an embodiment, parts 150, 152, 156, and a portion of part 158, herein, referred to as the "interior receptacle parts", are those parts, or parts of parts, which are contained within the interior receptacle. The adjustable screw further has an elongated screw portion 154 for rotatable engagement with another device, a head region with worm screw 152, and gear 156, and adjustment rod 158. The interior receptacle parts fit within the interior receptacle 134. As shown in FIGS. 3B and 3C, the viewer should be able to appreciate that the screw of FIG. 3B is positioned directly above its actual position in the device shown in FIG. 3C, when put together. The internal receptacle has two entry/exit portals, the first being adapted for the adjustment rod 158, and the second being adapted for the screw portion 168 of the adjustment screw. In this manner, the screw is held in place within the inner receptacle of the lower piece 130 (and similarly, or instead, within a corresponding inner receptacle of the upper piece 120).

Now skipping to FIG. 8, before returning to discuss FIGS. 4-7, FIG. 8A shows a perspective view of an adjustment rod, adjustment gear, worm screw, and adjustment screw, engaged with each other, in an embodiment of the disclosed technology. FIG. 8B shows a side view of the items shown in FIG. 8A. FIG. 8C shows a close-up perspective view of the adjustment rod of FIGS. 8A and 8B. FIG. 8D shows a side view of the adjustment screw of FIGS. 8A and 8B. The adjustment screw 200, which has a rod 230, in an embodiment of the disclosure, has any one of, or all, the following features. There is an upper ridge 238 and portal 235, such as a slit, square, plus, or other shaped portal to aid in abutment of a tool to adjust (turn) the rod 230. In this manner, gear 210, which is fixed in position with respect to the adjustment rod 230, turns, thus rotating the worm gear 220, the worm gear being engaged with the teeth 207 of the gear 210 (within the inner receptacle of either the lower or upper pieces 120 and/or 130). This causes the screw threading 225/205 to rotate, the rotation of the screw shaft causing the entire piece (including an entire upper piece 120 or lower piece 130) to move (shorten or lengthen/move closer or further away) from another portion of the adjustable prosthesis.

Turning now to the interior of the upper portion of the prosthesis, FIG. 4A is a side view of a cover of a vertical (upper) portion of an adjustable joint of embodiments of the disclosed technology. FIG. 4B is a side view of the vertical portion of the adjustable joint of FIG. 4A. FIG. 4C is a top view of the vertical portion of the adjustable joint of FIG. 4B. In the upper piece 120, there are a hollow interior space 126, dovetail 128, threaded portal 124 for engagement with the threading 225 of adjustment screw 200 (by way of example), and back plate 140 of the middle section of the prosthesis. The other elements have otherwise been described above; however, it should be understood that the interior space 126 receives the elongated portion (such as the threaded portion) of a screw, such a screw being associated with the lower piece 130. When the lower portion of the prosthesis is fully retracted, the screw, in an embodiment of the disclosed technology, reaches to near the end (within 1 cm) or to the end (within 0.2 mm) of the interior space, the end being at the right, in FIG. 4B.

FIG. 5 shows the interior portions of the upper housing, with cover removed. FIG. 5A shows a top view of the vertical portion of the adjustable joint, in an embodiment of the disclosed technology. FIG. 5B is a side view of a vertical screw of an embodiment of the disclosed technology, aligned with a corresponding receptacle of FIG. 5C. FIG. 5C is a side cutaway view of the vertical portion of the adjustable joint of FIG. 4B. FIG. 5D is a side cutaway view of the vertical portion of the adjustable joint, turned 90 degrees with respect to FIG. 5C. FIG. 5E is a side view of the vertical screw of FIG. 5B, aligned with the corresponding receptacle and orientation shown with references to the adjacently pictured FIG. 5D. Looking from the top down (FIG. 5A), it can be appreciated that inner receptacle 124 is viewable through a portal into the hollow space 126. It should also be appreciated that the top, as seen in FIG. 5A, may be rectangular, as shown, or circular so that it may more easily be capped in order to prevent soft tissue ingrowth. An inserted screw 154 (corresponding to screw 200 of FIG. 8) is shown within the lower piece, above the back plate 131. The upper adjustable screw functions as described with reference to screw 200 of FIG. 8, although the dimensions are different, as the vertical portion 120 of the prosthesis is longer than the horizontal portion 130, in an embodiment of the disclosed technology. Threading 164 engages with housing 121 of the upper portion 120. The adjustment rod 168 extends out of the inner receptacle 124, the screw head 160 being held in place therein, though rotatable by way of rotating the adjustment rod 168, which in turn rotates the gear 166 and the worm gear on the screw itself. This mechanism has been described in greater detail above, with respect to FIG. 8.

Figure 6A:
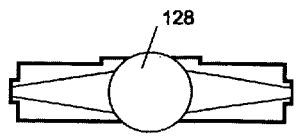
FIG. 6A shows a top view of a vertical housing of the vertical portion of the adjustable joint, in an embodiment of the disclosed technology.
Figure 6B:
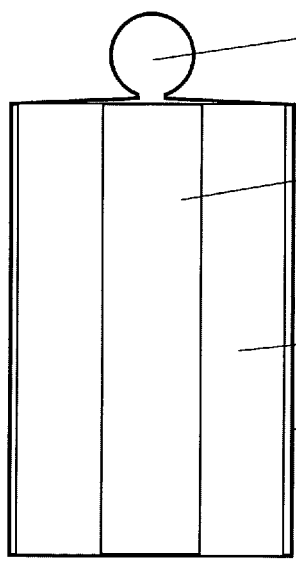
FIG. 6B shows a first side view of the vertical housing of FIG. 6A.
Figure 6C:
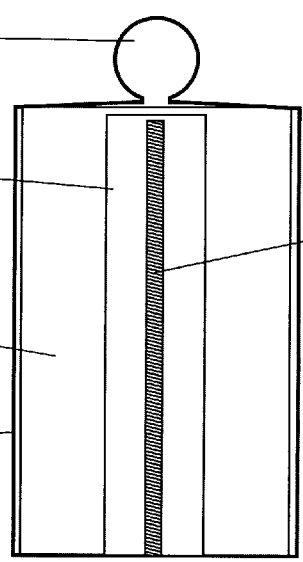
FIG. 6C shows a cutaway view of the first side view of the vertical housing of FIG. 6B.
Figure 6D:
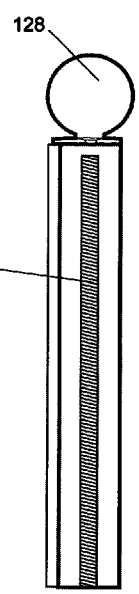
FIG. 6D shows a second side cutaway view of the vertical housing of FIGS. 6B and 6C.
Figure 6E:
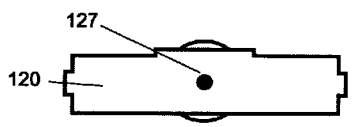
FIG. 6E shows a bottom view of the vertical housing of FIGS. 6A-6D.

FIG. 6A shows a top view of a vertical housing of the vertical portion of the adjustable joint, in an embodiment of the disclosed technology. FIG. 6B shows a first side view of the vertical housing of FIG. 6A. FIG. 6C shows a cutaway view of the first side view of the vertical housing of FIG. 6B. FIG. 6D shows a second side cutaway view of the vertical housing of FIGS. 6B and 6C. FIG. 6E shows a bottom view of the vertical housing of FIGS. 6A-6D. The ball (here, an oval shape) joint 128, in this embodiment, is integrated with the upper portion/vertical portion 120 of the prosthesis. The housing comprises a dovetail 129 for adjoining a connected piece (such as a rigid, stationary member held therein and forming a unitary structure with the middle piece 140), and has an interior cavity 126 for receiving an adjustable screw 164. Referring specifically to FIG. 6E, threaded portal 127 threadedly engages with the screw 164. In this manner, as the screw is adjusted (turned), it causes the screw to enter deeper in, or come further out of the interior space 126 of the upper piece 120. In this manner, the vertical portion of the prosthesis is elongated.

Figure 7A:
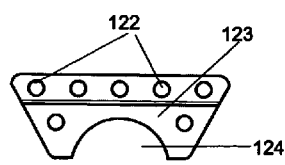
FIG. 7A shows a side view of a socket plate of an embodiment of the disclosed technology.
Figure 7B:
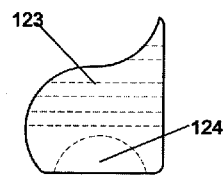
FIG. 7B shows a front view of the socket plate of FIG. 7A.
Figure 7C:
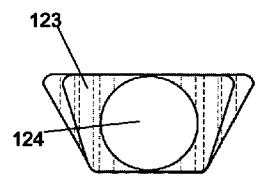
FIG. 7C shows a bottom view of the socket plate of FIGS. 7A and 7B.
Figure 8A:
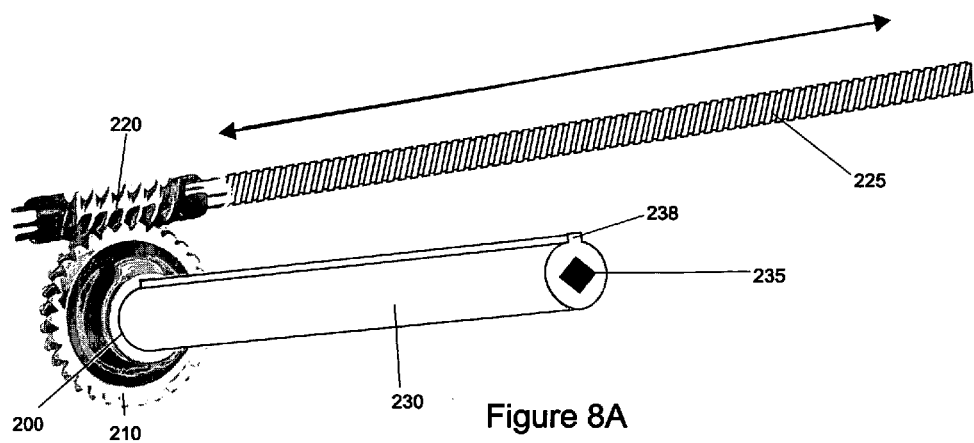
FIG. 8A shows a perspective view of an adjustment rod, adjustment gear, worm screw, and adjustment screw, engaged with each other, in an embodiment of the disclosed technology.
Figure 8B:
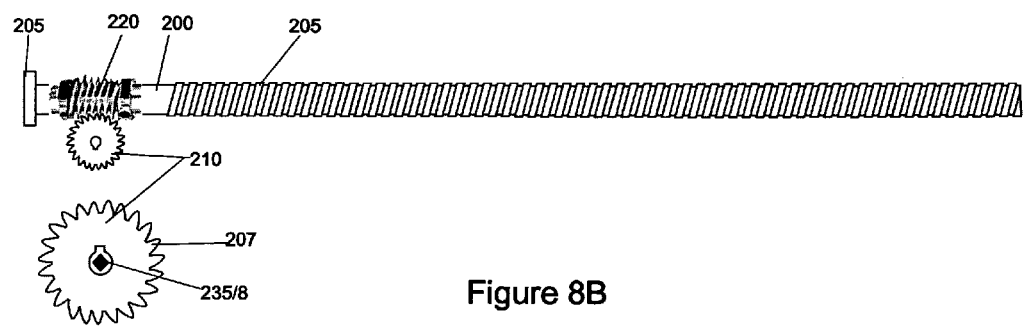
FIG. 8B shows a side view of the items shown in FIG. 8A.
Figure 8C:
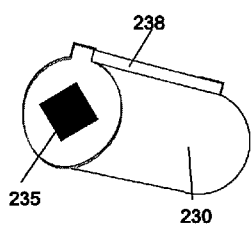
FIG. 8C shows a close-up perspective view of the adjustment rod of FIGS. 8A and 8B.
Figure 8D:
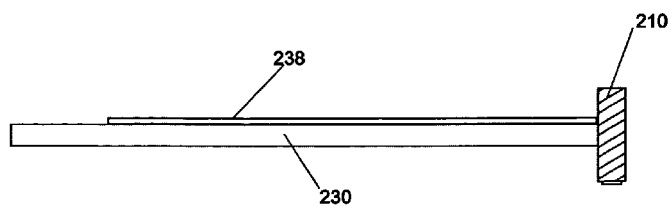
FIG. 8D shows a side view of the adjustment screw of FIGS. 8A and 8B.

FIG. 7A shows a side view of a socket plate of an embodiment of the disclosed technology. FIG. 7B shows a front view of the socket plate of FIG. 7A. FIG. 7C shows a bottom view of the socket plate of FIGS. 7A and 7B. The plate 123 has a plurality of portals 122 for attachment to bone, along with a portal to articulate with the a ball joint, such as ball joint 128 of the upper portion 130, shown in FIG. 6. This socket plate, of FIG. 7A-7C, corresponds to or replaces the function of the temporal bone condyle socket, or what is known as the "glenoid fossa" and this plate articulates with the skull.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods, systems, and devices described hereinabove are also contemplated and within the scope of the invention.

We claim:

1. A mandible prosthesis comprising:
   a prosthesis with adjustment mechanism located subperiosteal on the lateral side of said mandible;
   a portion of said prosthesis corresponding to a replaced portion of said mandible:
   a threaded, elongated member within said portion of said prosthesis;
   a gear functionally engaged between an adjustment rod of said adjustment mechanism and said threaded, elongated member arranged such that when said adjustment rod is rotated, said threaded, elongated member is rotated and an overall length of said portion of said prosthesis corresponding to said replaced portion of said mandible is increased or decreased, said mandible prosthesis further comprising at least one socket plate adapted for attachment of said prosthesis to bone and at least one ball joint engaged with said socket plate and said portion of said prosthesis corresponding to said portion of said mandible being replaced, wherein said ball joint is adapted to allow rotation of said portion of said prosthesis with respect to said socket plate.

2. The mandible prosthesis of claim 1, wherein said portion of said prosthesis corresponding to a portion of said mandible being replaced comprises a diagonal portion of said prosthesis corresponding to at least a ramus of said mandible;
   wherein said diagonal portion of said prosthesis increases in length upon rotation of said adjustment rod.

3. The mandible prosthesis of claim 2, further comprising a second portion of said prosthesis corresponding to a lower jaw, and a second adjustment mechanism, wherein when an adjustment rod of said second adjustment mechanism is rotated, said second portion of said prosthesis increases in length.

4. A mandible prosthesis comprising:
   a prosthesis with adjustment mechanism located subperiosteal on the lateral side of said mandible:
   a portion of said prosthesis corresponding to a replaced portion of said mandible:
   a threaded, elongated member within said portion of said prosthesis:
   a gear functionally engaged between an adjustment rod of said adjustment mechanism and said threaded, elongated member arranged such that when said adjustment rod is rotated, said threaded, elongated member is rotated and an overall length of said portion of said prosthesis corresponding to said replaced portion of said mandible is increased or decreased, wherein said threaded, elongated member comprises a worm screw engaged with said gear, said gear being fixed to said adjustment rod of said adjustment mechanism, wherein upon rotation of said adjustment rod, said worm gear and said threaded, elongated member rotate transverse to the direction of rotation of said adjustment rod and
   wherein a portion of said threaded shaft is housed within an outer housing of said prosthesis, and rotation of said threaded shaft causes said outer housing to move nearer or further away from another portion of said prosthesis, to which said threaded shaft is threadedly engaged.

5. The mandible prosthesis of claim 4, wherein a stop forms a unitary structure with said threaded shaft, and said stop and a portion said elongated shaft are held in place inside a cavity of said outer housing during elongation of said prosthesis.

6. A mandible prosthesis comprising:
   a prosthesis with adjustment mechanism located subperiosteal on the lateral side of said mandible:
   a portion of said prosthesis corresponding to a replaced portion of said mandible:
   a threaded, elongated member within said portion of said prosthesis:
   a gear functionally engaged between an adjustment rod of said adjustment mechanism and said threaded, elongated member arranged such that when said adjustment rod is rotated, said threaded, elongated member is rotated and an overall length of said portion of said prosthesis corresponding to said replaced portion of said mandible is increased or decreased, said mandible prosthesis comprising a diagonal portion corresponding to the mandibular ramus with adjustable screw therein, and lateral portion corresponding to a the body of the mandible or lower jaw bone, an adjustable screw therein, a unitary plate extending the length of said lateral portion and extending through a mid-portion corresponding at least to an angle of said mandible, wherein a first said adjustable screw extends a housing of said diagonal portion past an elongated, planar surface of said unitary plate, and a second said adjustable screw extends a housing said lower portion past an elongated, planar surface of said unitary plate.

7. The mandible prosthesis of claim 6, wherein each said housing comprises a first cavity comprising a majority of said elongated, threaded member therein.

8. The mandible prosthesis of claim 7, wherein each said housing further comprises a second cavity with an internal area adapted to retain a stop of said elongated, threaded member therein, and consists of two portals, a first said portal adapted for passage there-through of said elongated, threaded member, and a second said portal adapted for passage there-through of said adjustment rod.

* * * * *